United States Patent [19]

Peters et al.

[11] Patent Number: 5,077,806

[45] Date of Patent: Dec. 31, 1991

[54] MACHINE VISION ANALYSIS APPARATUS

[75] Inventors: Richard K. Peters; Donald V. Elmerick, Tallmadge; James L. Spayer, Brecksville; Gerald E. Walter, Cleveland, all of Ohio

[73] Assignee: Accuron Corporation, Cleveland, Ohio

[21] Appl. No.: 360,221

[22] Filed: Jun. 1, 1989

[51] Int. Cl.⁵ .............................................. G06K 9/00
[52] U.S. Cl. ........................................ 382/8; 382/1; 358/101; 358/106; 358/107
[58] Field of Search ................. 382/8, 41, 48, 50, 51; 358/464, 465, 466, 88, 101, 106, 107

[56] References Cited

U.S. PATENT DOCUMENTS

| | | | |
|---|---|---|---|
| 2,965,703 | 12/1960 | Loughlin | 356/526 |
| 3,804,531 | 4/1974 | Kosaka et al. | 356/176 |
| 3,935,436 | 1/1976 | Holschlag | 356/96 |
| 4,029,419 | 6/1977 | Schumann, Jr. et al. | 356/173 |
| 4,175,860 | 11/1979 | Bacus | 356/39 |
| 4,253,766 | 3/1981 | Funk | 356/418 |
| 4,402,611 | 9/1983 | Yuasa | 356/405 |
| 4,412,744 | 11/1983 | Lee et al. | 356/319 |
| 4,420,742 | 12/1983 | Tadauchi et al. | 358/464 |
| 4,464,054 | 8/1984 | Karras et al. | 356/406 |
| 4,491,962 | 1/1985 | Sakou et al. | 382/50 |
| 4,505,589 | 3/1985 | Ott et al. | 356/402 |
| 4,518,258 | 5/1985 | Broersma | 356/405 |
| 4,527,897 | 7/1985 | Okabe | 356/407 |
| 4,539,647 | 9/1985 | Kaneko et al. | 364/526 |
| 4,550,435 | 10/1985 | Hayman | 382/50 |
| 4,578,711 | 3/1986 | White et al. | 358/464 |
| 4,581,762 | 4/1986 | Lapidus et al. | 382/8 |
| 4,583,858 | 4/1986 | Lebling et al. | 356/402 |
| 4,596,037 | 6/1986 | Bouchard et al. | 382/8 |
| 4,635,213 | 1/1987 | Murata et al. | 364/526 |
| 4,653,014 | 3/1987 | Mikami et al. | 364/526 |
| 4,678,338 | 7/1987 | Kitta et al. | 356/402 |
| 4,692,481 | 9/1987 | Kelly | 356/402 |
| 4,707,138 | 11/1987 | Coatney | 356/402 |
| 4,715,715 | 12/1987 | Howarth et al. | 356/402 |
| 4,723,174 | 2/1988 | Nishikawa et al. | 358/464 |
| 4,736,441 | 4/1988 | Hirose et al. | 382/48 |
| 4,776,024 | 10/1988 | Katch et al. | 382/9 |
| 4,807,762 | 2/1989 | Illy et al. | 356/425 |
| 4,853,793 | 8/1989 | Ishikawa et al. | 358/464 |
| 4,885,784 | 12/1989 | Miyagawa et al. | 358/464 |
| 4,959,869 | 9/1990 | Hongo | 382/50 |

OTHER PUBLICATIONS pp. 886–892 (copy) of article entitled—Automated Screening of Cervical Smears Using Immunocytochemical Staining: a Possible Approach.

pp. 241–254 (copy) from Gynecologic Oncology—article is entitled—Automated Quantitative Fluorescent Image Analysis of Cervical Cytology.

7 pages of article entitled—Image Analysis Combined with Quantitative Cytochemistry.

Primary Examiner—David K. Moore
Assistant Examiner—Jose L. Couso
Attorney, Agent, or Firm—Henderson & Sturm

[57] ABSTRACT

A machine vision analysis apparatus and method for automatically checking objects for specified characteristics. A video camera is provided for producing an analog video input signal corresponding to an area having an object therein being observed by the video camera. A video timer and synchronizer is used for coordinating synchronous operation of the machine vision apparatus. A digital-to-analog converter is also provided for converting a digital threshold gray level into an analog threshold level corresponding to said digital threshold level, wherein an upper and a lower threshold level are produced. A comparator is used for digitizing the analog video input signal into a digitized video signal based on the analog threshold gray levels, wherein the video input gray level must fall between the lower threshold gray level and the upper threshold gray level for a pixel to be digitized into an ON state. A pixel counter is used for summing the number of ON pixels in the digitized video signal within a predetermined portion of said video signal and produces a binary digital count output corresponding to the number of ON pixels. A microprocessor based digital control is used for analyzing and comparing said digital count output with expected and desired count results, and a program is provided for controlling operation of the microprocessor.

11 Claims, 3 Drawing Sheets

MACHINE VISION ANALYSIS APPARATUS

BACKGROUND OF THE INVENTION

I. Field of the Invention

This invention relates to a machine vision analysis apparatus which may by used to inspect the image of an object to determine if the object fulfills specified criteria, and where it is assumed in practice that if the image satisfies the representative criteria, the object satisfies the actual physical requirements of which the criteria are representative.

II. Background of the Invention

Inspection of materials, objects, and constructions is required in many of today's industries, whether it by the inspection of an auto part coming off the assembly line or a microscopic inspection of a pap smear. This repetitive analysis often requiring exact attention is usually tedious and therefore is susceptible to human error. Whether the error be caused by laziness or fatigue is inconsequential, the fact is that personal inspection of a repetitive nature should be avoided wherever possible.

While the prior art is replete with myriad and diverse machine vision systems, the typical system is overly complex and unnecessarily limited in its scope of application. In general, the prior art constructions include a system for complex analysis of an input provided by a single video camera. This complexity increases the cost of such a vision system, and the cost prohibits the widespread application of such a system despite its useful application.

In addition, on an assembly line more than one view of an object may require inspection or the proximity of several lines may facilitate the combination of analysis hardware for both inspections. However, the prior art does not provide for such a combination and the expensive analysis hardware must be duplicated despite the close proximity of target objects. This required duplication of expensive equipment, such as microprocessors or personal computers, and therefore adds to the generally prohibitive cost of such vision analysis systems.

SUMMARY OF THE INVENTION

The present invention relates to a machine vision analysis apparatus and method for automatically checking objects for specified characteristics. A video camera is provided for producing an analog video input signal corresponding to an area having an object therein being observed by the video camera. A video timer and synchronizer is used for coordinating synchronous operation of the machine vision apparatus. A digital-to-analog converter is also provided for converting a digital threshold gray level into an analog threshold level corresponding to said digital threshold level, wherein an upper and a lower threshold level are produced. A comparator is used for digitizing the analog video input signal into a digitized video signal based on the analog threshold gray levels, wherein the video input gray level must fall between the lower threshold gray level and the upper threshold gray level for a pixel to be digitized into an ON state. A pixel counter is used for summing the number of ON pixels in the digitized video signal within a predetermined portion of said video signal and produces a binary digital count output corresponding to the number of ON pixels. A microprocessor based digital control is used for analyzing and comparing said digital count output with expected and desired count results, and a program is provided for controlling operation of the microprocessor.

A image window generator may be used to focus the analysis of the system on a sub-area of interest which contains an object to be inspected through its video representation.

In addition, a second video camera may be provided, along with a second window comparator, a second counter, a second image window generator, and a control toggle and analog switch to alternate between the pair of camera inputs.

An object of the present invention is to provide an improved method and apparatus for machine vision analysis.

Another object of the present invention is to provide a method and apparatus of the aforementioned type which includes the capability of having two video cameras and handling two input video signals.

A still further object of the present invention is to provide a method and apparatus for machine vision analysis which facilitates the limiting of the analysis of an input signal to a designated area within the entire signal area where an object of interest will be found.

Other objects, advantages and novel features of the invention will become apparent from the following detailed description of the invention when considered in conjunction with the accompanying drawings.

BEST MODES FOR CARRYING OUT THE INVENTION

Figure 1:
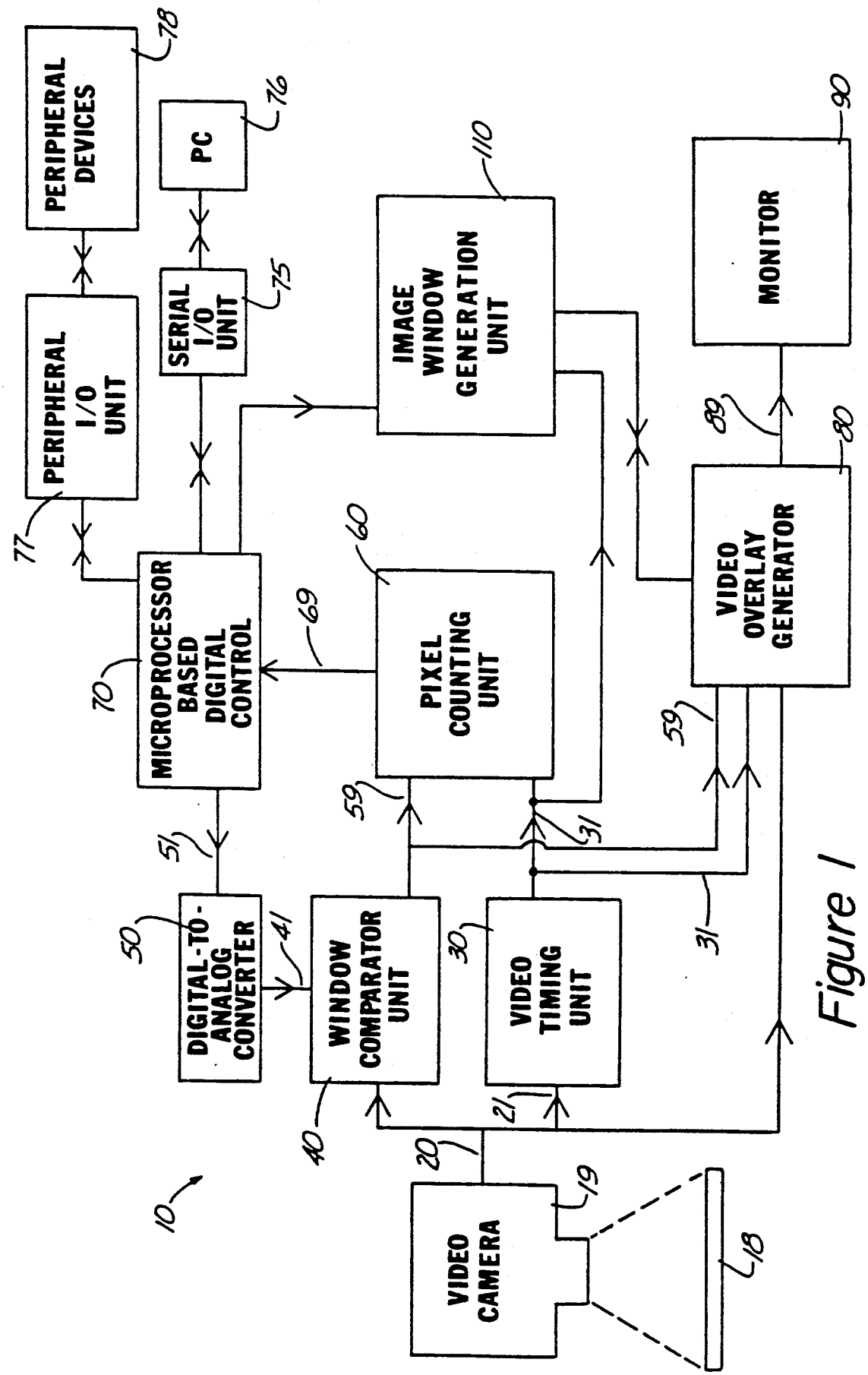
FIG. 1 is a schematic diagram of the machine vision analysis apparatus.

Referring now to the drawings wherein like reference numerals designate identical or corresponding parts throughout the several views, FIG. 1 shows a machine vision analysis apparatus (10) constructed in accordance with the present invention.

A video camera (19) has an analog signal output (20) which constitutes an input into a video timing unit (30) and a window comparator unit (40). The video timing unit (30) is provided to synchronize the operation of various functions of the apparatus (10). The window comparator unit (40) is provided for transforming the video input signal (20) into a digitized output signal (41) representative of the video image seen by the camera. A digital-to-analog converter (50) is utilized to transform digital gray level threshold inputs (51) into analog gray level threshold outputs (41) for use by the window comparator unit (40).

A pixel counter (60) is employed to count the occurrence of digitized pixels; that is, pixels within the desired gray level range. A microprocessor based digital control configuration (70) receives the output (69) of the pixel counting unit (60), and the microprocessor configuration (70) is utilized to perform analyses on the output (69) to determine if the observed object (18) fulfills desired requirements. The microprocessor configuration (70) is further utilized to set the acceptable gray level ranges for the window comparator unit (40) through use of microprocessor outputs (51) and the digital-to-analog converter (50). In general, the microprocessor configuration (70) is provided with a computer program to lead the microprocessor through the steps of its operation and analysis.

A video overlay unit (80) highlights the area of the input video image under analysis and darkens pixels found to be ON during the digitization process. This overlay unit (80) clearly illustrates to a user the area under analysis as well as the portions digitized by the current threshold gray levels.

The video input signal (20) includes standard timing signals for horizontal and vertical synchronization of the incoming video signal, and referring to FIG. 1, it should be appreciated that the video timing unit (30) receives the horizontal synchronization and the vertical synchronization signals (21). These synchronization signals (21) are then output as synchronization signals (31) to those portions of the machine vision analysis apparatus (10) which utilize such synchronization information, such as the pixel counter unit (60) and the video overlay unit (80).

Still referring to FIG. 1, the window comparator unit (40) of the analysis apparatus (10) is a comparator configuration consisting of an analog video input signal (20) as well as an upper threshold voltage and a lower threshold voltage. These thresholds are received from the digital-to-analog converter device (50) through input lines (41). The window comparator unit (40) is designed to digitize the video signal (20) from analog form, into a digitized form where each pixel may be only ON or OFF.

The purpose of the window comparator unit (40) is to make the decision of whether a pixel is ON or OFF. This determination is made by comparing the pixel gray level of the video input (20) to the threshold gray levels. In general, if the input gray level (20) is greater than the lower threshold gray level and less than the upper threshold gray level, the output will indicate that the current pixel of the input signal (20) is ON. Otherwise, the pixel is indicated to be OFF.

The digital-to-analog converter (50) of FIG. 1 comprises a standard D/A converter which receives digital information from the microprocessor based digital control configuration (70) through input lines (51) and outputs an analog voltage on output lines (41).

In general, the input digital information (51) to the D/A converter (50) from the microprocessor configuration (70) includes the digital gray level representation of the upper or lower thresholds as well as address information to indicate which threshold is currently being provided. The converter (50) then provides the analog threshold to the appropriate threshold input of the window comparator unit (40).

Still referring to FIG. 1, it may be appreciated that the pixel counting unit (60) provides a way to count the occurrences of ON pixels from the window comparator unit (40) in the digitized signal output (59). The output count (69) of the pixel counting unit (60) is accepted by the microprocessor control configuration (70). The pixel count output (69) is, in general, provided to the microprocessor configuration (70) at the end of each horizontal line of the digitized signal (59). However, the counter arrangement may vary so that the count will be provided at any desired interval to the microprocessor (70).

The pixel counting unit (60) further receives an input signal (31) from the video timing unit (30). This input signal (31) serves to synchronize the counting unit (60) with the video input (20) such that the pixel count conforms to the desired counting interval, whether that interval be one horizontal line or one entire frame.

Figure 2:
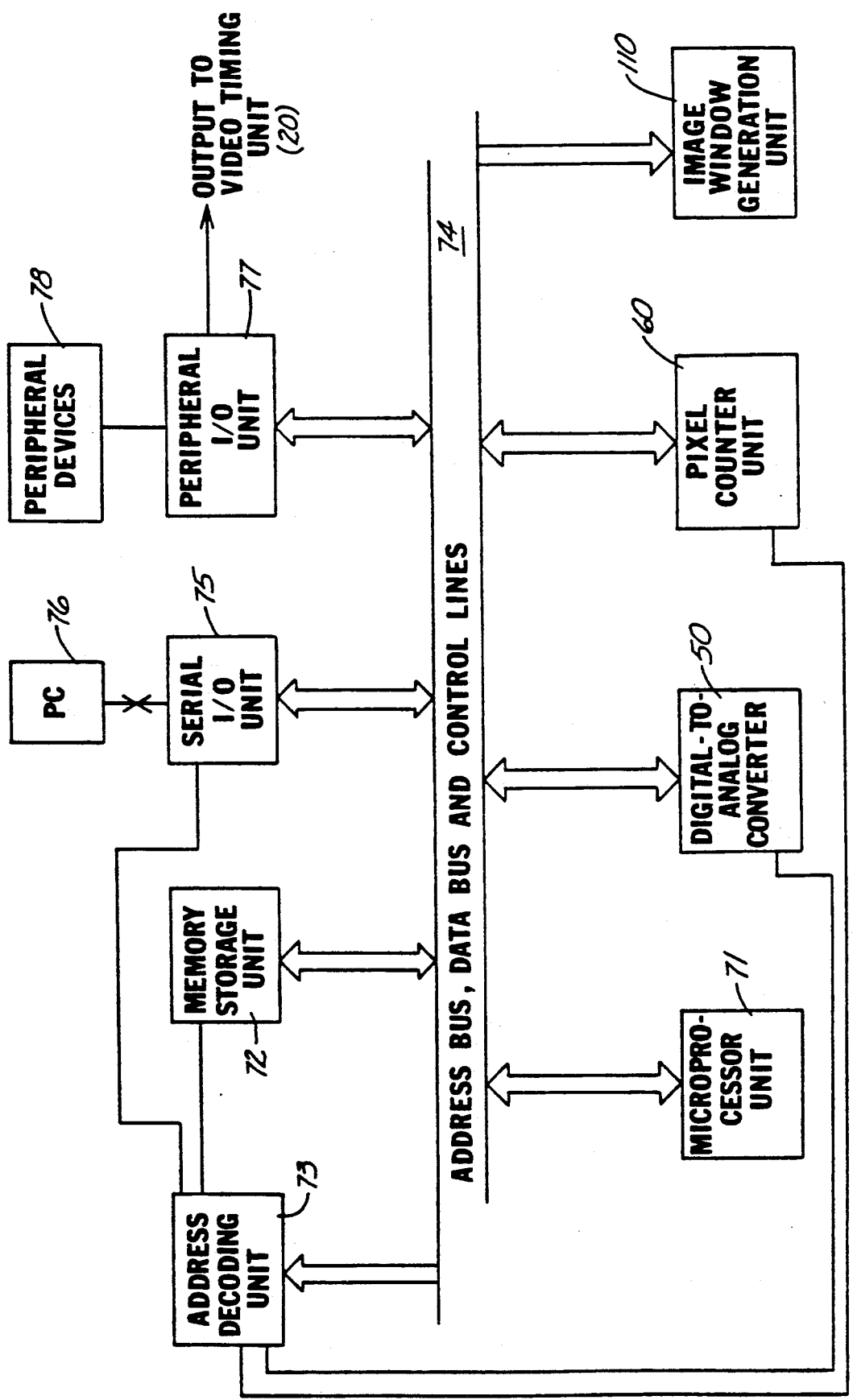
FIG. 2 is a schematic diagram showing the microprocessor control configuration in conjunction with its input and output lines; and, FIG. 3 is a schematic diagram of an alternate machine vision analysis apparatus.

Turning now to FIG. 2, the microprocessor based digital control configuration (70) includes a microprocessor unit (71) for performing required control and analysis operations of the machine vision analysis apparatus (10) of FIG. 1. As is well known, the control and analysis operations are put into a program form which controls the microprocessor unit (71), and the microprocessor unit (71) in turn uses this program to function as the controlling force for the apparatus (10).

A memory storage configuration (72) is utilized to store these operating instructions as well as data pertinent to the desired analysis. In general, the memory storage unit will include a combination of random access memory (RAM) units and read only memory (ROM) units.

The address decoding unit (73) employed to multiplex the address lines into control lines for signalling a device that it should send or receive information on the data bus (74). In general, the address decoding unit (73) will send control signals to the individual memory units, the serial input/output unit (75), the digital-to-analog converter unit (50), and the pixel counter unit (60).

The serial input/output unit (75) of the microprocessor configuration (70) comprises a standard serial data interchange configuration such that data may be serially received to or transmitted from the microprocessor unit (71). Typically, a standard RS-232 serial port or RS-422 port is utilized for the interchange of data. This serial data exchange unit (75) is provided to allow an independent personal computer (76) or similar external computing device access the microprocessor unit (71). In this way, the characteristics controlling operation of the machine vision analysis apparatus (10) may be controlled and programmed into the apparatus (10) through the use of external computing devices.

The microprocessor configuration (70) may include a peripheral input/output unit (77) to facilitate the interchange of signals and information as needed with external peripheral devices (78). For instance, an external electric eye may be configured so as to signal to the microprocessor unit (71) through the peripheral input/output unit (77) that an object is in position to be analyzed. Similarly, if the object (18) under observation fails to meet (as determined by the microprocessor and its program specifications) established requirements, then a fail signal may be produced and output through the peripheral input/output unit (77) to cause the failed object to be removed from the assembly line.

Still refering to FIG. 1, the video overlay unit (80) is provided to produce an especially useful output form of the input video signal (20). The video overlay unit (80) receives the input video signal (20) from the video camera unit, as well as inputs (31) and (59) from the window comparator unit (40) and the video timing unit (30). The output (89) of the video overlay unit (80) is a standard video signal having various pixels modified; the output (89) will in general be provided to a monitor unit (90) for display of the output video signal (89).

The video overlay unit (80) operates in such a fashion that all pixels which are being subjected to the digitization scheme will be slightly altered. This alteration is different for ON pixels than what it is for OFF pixels. The video overlay output unit (80) produces this alteration by applying an offset voltage to the pixels which are undergoing gray level analysis and digitization. This offset voltage will increase the gray level of the pixel. If the pixel is found to be ON in the digitization, the offset will be greater than if it is found to be OFF. In this way, the ON pixels will be darker pixels and this altered display may be used as a feedback mechanism by the operator in setting the appropriate gray level thresholds such that the areas of interest are digitized properly.

The monitor unit (90) utilized to display the output video signal (89) is a standard television monitor which will accept a standard video signal as an input and output that signal in visual form.

In general an object of interest in a video picture fills much less than the entire video area, thus an image window generation unit (110) is provided in this embodiment of the machine vision analysis apparatus (10). The image window generation unit (110) allows the image analysis to be limited to a sub-area of the entire video picture. In this way, only the sub-area of direct and significant importance is analyzed, thus allowing greater flexibility in the description of the analysis requirements.

The image window generation unit (110) receives an input (109) from the microprocessor configuration (70). This input (109) permits the microprocessor unit (71) to control the size and location of the image window. The desired size and location information are provided to the generation unit (110), which in turn uses those parameters and a series of timing mechanisms to generate the appropriate signals to the counter unit (60) and the video overlay unit (80) such that only digitized pixels within the image window will be summed and such that only pixels within the image window will be offset in any way at the video output (89). In this way, the analysis is effectively limited to the desired sub-area and the output video will clearly show the sub-area and the digitization within that sub-area, thus serving as a powerful feedback tool for the system operator.

Figure 3:
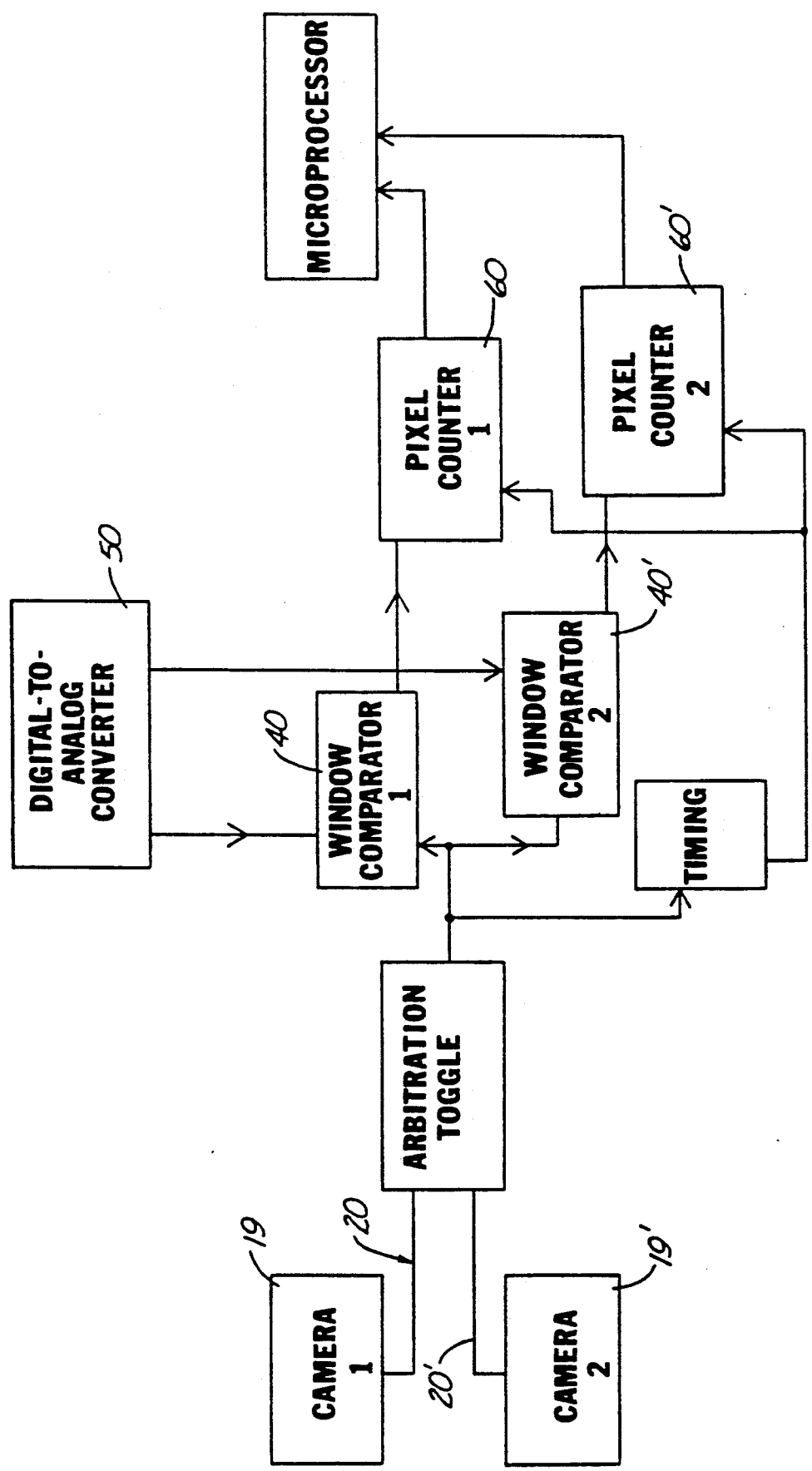

In the alternate embodiment of the present invention as shown in FIG. 3, the machine vision analysis apparatus (10) will include a second video camera (19') having an associated second analog signal output (20'). In addition, an arbitration unit (100) will be utilized to produce a control toggle signal to control which camera output is to be analyzed. The toggle signal controls an analog switch which alternates passing the video camera one output (20) and the video camera two output (20') to the window comparator unit (40) for digitizing. A second window comparator unit (40') is provided for digitizing the second input signal (20') based on distinct gray level thresholds set by the microprocessor. The digital-to-analog converter (50) is configured so as to provide the gray level thresholds for the first comparator (40) as well as the distinct gray level thresholds for the second comparator (40') as needed by the respective window comparator units (40) and (40').

Further, a second pixel counting unit (60') identical to the first pixel counting unit (60) except that the second counter (60') counts the active pixels as digitized by the second window comparator (40'). Just as in the case of single camera operation, the output of the second pixel counter (60') is routed to the microprocessor control unit (70) for analysis.

Accordingly, it will be appreciated that the preferred embodiment disclosed herein does indeed accomplish the aforementioned objectives. Obviously, many modifications and variations of the present invention are possible in light of the above teachings. It is therefore to be understood that, within the scope of the appended claims, the invention may be practiced otherwise than as specifically described.

We claim:

1. A machine vision analysis apparatus for automatically checking objects for specified characteristics, said machine vision apparatus comprising:

video camera means for producing an analog video input signal corresponding to an area having an object therein observed by said video camera means;

a video timing means adapted to synchronize both vertical and horizontal signals of said analog video input signal received from said video camera means and to provide a signal capable of synchronizing a counting unit with the video input such that the pixel count conforms to a desired counting interval;

a digital-to-analog converter means adapted to transform digital gray level threshold inputs into analog gray threshold outputs for use by a comparator means by receiving digital information from a microprocessor and then providing an analog voltage to a comparator means such that said analog voltage provides a gray level representation of at least one of an upper and lower threshold gray level as well as address information to indicate which of said upper or lower thresholds is provided;

a comparator means adapted to transform the analog video input signal into a digitized output signal representing the image viewed by said video camera means such that if the input gray level is greater than the lower threshold gray level and less than the upper gray level the digitized output of said comparator means will indicate that the current pixel of the analog video input signal is "ON";

pixel counting means adapted to count the occurence of digitized pixels within the desired gray threshold level by counting the occurence of "ON" pixels from said digitized output of said comparator means and sending said pixel count to a microprocessor based digital control means at the end of each horizontal line of said digitized output and to receive an input signal from said timing unit means which serves to syncronize the counting unit with the video unit such that the pixel count conforms to the desired counting interval;

microprocessor based digital control means adapted to receive output signals from said pixel counting means and to perform an analysis of the output to determine if the observed object fulfills desired requirements and to set the acceptable gray level ranges for said comparator means through use of microprocessor outputs and said digital-to-analog converter means.

2. The apparatus of claim 1 including image window generation means for limiting the size and location of a sub-area of a total image area being observed by the video camera means and producing control signals such that the summing of active pixels will occur only within portions of said image window, and where said size and location limitations are provided by said microprocessor control means.

3. The apparatus of claim 1 wherein the microprocessor based digital control means includes a serial input/output means for communicating with an external device.

4. The apparatus of claim 1 wherein the microprocessor based digital control means includes a peripheral input/output means for communicating with an array of peripheral devices.

5. The apparatus of claim 1 wherein the machine vision apparatus further comprises:
   a second video camera means for producing a second analog video input signal corresponding to a second area having an object therein being observed by said video camera means;
   said digital-to-analog converter including means for providing a second set of analog threshold levels to a second comparator means;
   a second comparator means for digitizing said second analog video input signal into a second digitized video signal based on said second analog threshold gray levels, where said second video input pixel gray level must fall between the second lower threshold gray level and the second upper threshold gray level for the pixel to be digitized into an ON state;
   second pixel counting means for summing the number of ON pixels in said second digitized video signal within a predetermined portion of said second digitized video signal and producing a second digitized count output corresponding to said number of ON pixels;
   said microprocessor based digital control including means for analyzing and comparing said second as well as said first digitized count output with expected and desired count results.

6. The apparatus of claim 5 including image window generation means for limiting the size and location of a sub-area of a total image area being observed by the first or second video camera means and producing control signals such that the summing of active pixels will occur only within portions of said image window, and where said size and location limitations are independent for each said first and said second video camera inputs and are provided by said microprocessor control means.

7. The apparatus of claim 5 wherein the microprocessor based digital control means includes a serial input/output means for communicating with an external computing device.

8. The apparatus of claim 5 wherein the microprocessor based digital control means includes a peripheral input/output means for communicating with an array of peripheral devices.

9. The apparatus of claim 1 wherein the microprocessor based digital control means includes an address decoding means for decoding address lines to produce control signals.

10. The apparatus of claim 1 wherein the microprocessor based digital control means includes a memory storage means.

11. The apparatus of claim 10 wherein the memory storage means include at least one random access memory means and at least one read only memory means.

* * * * *